(12) United States Patent
Parker

(10) Patent No.: US 11,766,566 B2
(45) Date of Patent: *Sep. 26, 2023

(54) IMPLANTED PULSE GENERATORS WITH REDUCED POWER CONSUMPTION VIA SIGNAL STRENGTH/DURATION CHARACTERISTICS, AND ASSOCIATED SYSTEMS AND METHODS

(71) Applicant: Nevro Corp., Redwood City, CA (US)

(72) Inventor: Jon Parker, San Jose, CA (US)

(73) Assignee: Nevro Corp., Redwood City, CA (US)

( * ) Notice: Subject to any disclaimer, the term of this patent is extended or adjusted under 35 U.S.C. 154(b) by 92 days.

This patent is subject to a terminal disclaimer.

(21) Appl. No.: 17/114,314

(22) Filed: Dec. 7, 2020

(65) Prior Publication Data
US 2021/0220649 A1    Jul. 22, 2021

Related U.S. Application Data

(63) Continuation of application No. 16/183,456, filed on Nov. 7, 2018, now Pat. No. 10,881,857, which is a (Continued)

(51) Int. Cl.
*A61N 1/36* (2006.01)
*A61N 1/37* (2006.01)

(52) U.S. Cl.
CPC ..... *A61N 1/36071* (2013.01); *A61N 1/36125* (2013.01); *A61N 1/36171* (2013.01); *A61N 1/36175* (2013.01); *A61N 1/3708* (2013.01)

(58) Field of Classification Search
CPC ............ A61N 1/36071; A61N 1/36125; A61N 1/36171; A61N 1/36175; A61N 1/3708
See application file for complete search history.

(56) References Cited

U.S. PATENT DOCUMENTS 3,774,618 A   11/1973   Avery
3,871,382 A   3/1975    Mann
(Continued)

FOREIGN PATENT DOCUMENTS

EP   0754437   1/1997
EP   1610437   12/2005
(Continued)

OTHER PUBLICATIONS

North et al., "Spinal Cord Stimulation for Axial Low Back Pain," Spine, vol. 30, No. 12, 2005, 7 pages.
(Continued)

*Primary Examiner* — George Manuel
(74) *Attorney, Agent, or Firm* — Perkins Coie LLP

(57) ABSTRACT

Implanted pulse generators with reduced power consumption via signal strength-duration characteristics, and associated systems and methods are disclosed. A representative method for treating a patient in accordance with the disclosed technology includes receiving an input corresponding to an available voltage for an implanted medical device and identifying a signal delivery parameter value of an electrical signal based on a correlation between values of the signal delivery parameter and signal deliver amplitudes. The signal deliver parameter can include at least one of pulse width or duty cycle. The method can further include delivering an electrical therapy signal to the patient at the identified signal delivery parameter value using a voltage within a margin of the available voltage.

23 Claims, 7 Drawing Sheets

Related U.S. Application Data continuation of application No. 15/227,821, filed on Aug. 3, 2016, now Pat. No. 10,173,062, which is a continuation of application No. 14/710,375, filed on May 12, 2015, now Pat. No. 9,409,020.

(60) Provisional application No. 62/000,985, filed on May 20, 2014.

(56) References Cited

U.S. PATENT DOCUMENTS

| | | |
|---|---|---|
| 4,014,347 A | 3/1977 | Halleck et al. |
| 4,071,032 A | 1/1978 | Schulman |
| 4,072,154 A | 2/1978 | Anderson |
| 4,082,097 A | 4/1978 | Mann et al. |
| 4,197,850 A | 4/1980 | Schulman et al. |
| 4,230,121 A | 10/1980 | Stanton |
| 4,441,498 A | 4/1984 | Nordling |
| 4,479,489 A | 10/1984 | Tucci |
| 4,556,063 A | 12/1985 | Thompson |
| 4,632,117 A | 12/1986 | James |
| 4,636,706 A | 1/1987 | Bowman et al. |
| 4,642,479 A | 2/1987 | Lombardi |
| 4,890,616 A | 1/1990 | Pinckaers |
| 5,042,486 A | 8/1991 | Pfeiler et al. |
| 5,052,375 A | 10/1991 | Stark et al. |
| 5,065,083 A | 11/1991 | Owens |
| 5,078,140 A | 1/1992 | Kwoh |
| 5,144,946 A | 9/1992 | Weinberg et al. |
| 5,211,165 A | 5/1993 | Dumoulin et al. |
| 5,257,636 A | 11/1993 | White |
| 5,279,292 A | 1/1994 | Baumann et al. |
| 5,325,873 A | 7/1994 | Hirsch et al. |
| 5,375,596 A | 12/1994 | Twiss et al. |
| 5,425,367 A | 6/1995 | Shapiro et al. |
| 5,591,212 A | 1/1997 | Keimel |
| 5,643,330 A | 7/1997 | Holsheimer et al. |
| 5,679,026 A | 10/1997 | Fain et al. |
| 5,727,553 A | 3/1998 | Saad |
| 5,733,313 A | 3/1998 | Barreras, Sr. et al. |
| 5,755,743 A | 5/1998 | Volvz et al. |
| 5,782,880 A | 7/1998 | Lahtinen |
| 5,807,397 A | 9/1998 | Barreras |
| 5,871,487 A | 2/1999 | Warner et al. |
| 5,893,883 A | 4/1999 | Torgerson |
| 5,916,237 A | 6/1999 | Schu |
| 5,929,615 A | 7/1999 | D'Angelo |
| 5,983,141 A | 11/1999 | Sluijter et al. |
| 6,076,018 A | 6/2000 | Sturman et al. |
| 6,115,634 A | 9/2000 | Donders et al. |
| 6,167,303 A | 12/2000 | Thompson |
| 6,185,452 B1 | 2/2001 | Schulman et al. |
| 6,185,454 B1 | 2/2001 | Thompson |
| 6,192,278 B1 | 2/2001 | Werner et al. |
| 6,198,963 B1 | 3/2001 | Haim et al. |
| 6,223,080 B1 | 4/2001 | Thompson |
| 6,236,888 B1 | 5/2001 | Thompson |
| 6,323,603 B1 | 11/2001 | Persson |
| 6,324,426 B1 | 11/2001 | Thompson |
| 6,387,332 B1 | 5/2002 | Dickinson |
| 6,434,425 B1 | 8/2002 | Thompson |
| 6,438,418 B1 | 8/2002 | Swerdlow et al. |
| 6,440,090 B1 | 8/2002 | Schallhorn |
| 6,453,198 B1 | 9/2002 | Torgerson et al. |
| 6,472,991 B1 | 10/2002 | Schulman et al. |
| 6,474,341 B1 | 11/2002 | Hunter et al. |
| 6,496,729 B2 | 12/2002 | Thompson |
| 6,516,227 B1 | 2/2003 | Meadows et al. |
| 6,553,263 B1 | 4/2003 | Meadows et al. |
| 6,650,943 B1 | 11/2003 | Whitehurst et al. |
| 6,712,772 B2 | 3/2004 | Cohen et al. |
| 6,757,561 B2 | 6/2004 | Rubin et al. |
| 6,812,708 B2 | 11/2004 | Bristol |
| 6,862,480 B2 | 3/2005 | Cohen et al. |
| 6,871,090 B1 | 3/2005 | He et al. |
| 6,871,099 B1 | 3/2005 | Whitehurst et al. |
| 6,875,571 B2 | 4/2005 | Crabtree et al. |
| 6,909,915 B2 | 6/2005 | Greatbatch |
| 6,950,707 B2 | 9/2005 | Whitehurst |
| 7,020,523 B1 | 3/2006 | Lu et al. |
| 7,027,860 B2 | 4/2006 | Bruninga et al. |
| 7,054,689 B1 | 5/2006 | Whitehurst et al. |
| 7,082,333 B1 | 7/2006 | Bauhahn et al. |
| 7,120,499 B2 | 10/2006 | Thrope et al. |
| 7,127,288 B2 | 10/2006 | Sturman et al. |
| 7,142,923 B2 | 11/2006 | North et al. |
| 7,167,749 B2 | 1/2007 | Biggs et al. |
| 7,167,756 B1 | 1/2007 | Torgerson et al. |
| 7,177,690 B2 * | 2/2007 | Woods ............... A61N 1/3787 607/33 |
| 7,177,703 B2 | 2/2007 | Boveja et al. |
| 7,180,760 B2 | 2/2007 | Varrichio et al. |
| 7,184,836 B1 | 2/2007 | Meadows et al. |
| 7,206,642 B2 | 4/2007 | Pardo et al. |
| 7,209,792 B1 | 4/2007 | Parramon et al. |
| 7,212,867 B2 | 5/2007 | Van Venrooij et al. |
| 7,236,834 B2 | 6/2007 | Christopherson et al. |
| 7,241,283 B2 | 7/2007 | Putz |
| 7,244,150 B1 | 7/2007 | Brase et al. |
| 7,254,449 B2 | 8/2007 | Karunasiri |
| 7,266,412 B2 | 9/2007 | Stypulkowski |
| 7,313,440 B2 | 12/2007 | Miesel |
| 7,329,262 B2 | 2/2008 | Gill |
| 7,337,010 B2 | 2/2008 | Howard et al. |
| 7,381,441 B2 | 6/2008 | Leung et al. |
| 7,425,142 B1 | 9/2008 | Putz |
| 7,437,193 B2 | 10/2008 | Parramon et al. |
| 7,489,968 B1 | 2/2009 | Alexander et al. |
| 7,571,002 B2 | 8/2009 | Thrope et al. |
| 7,606,622 B2 | 10/2009 | Reeve |
| 7,616,990 B2 | 11/2009 | Chavan et al. |
| 7,636,602 B2 | 12/2009 | Baru Fassio et al. |
| 7,641,992 B2 | 1/2010 | Howard et al. |
| 7,650,191 B1 | 1/2010 | Lim et al. |
| 7,682,745 B2 | 3/2010 | Howard et al. |
| 7,697,984 B2 | 4/2010 | Hill et al. |
| 7,702,379 B2 | 4/2010 | Avinash et al. |
| 7,769,462 B2 | 8/2010 | Meadows et al. |
| 7,801,615 B2 | 9/2010 | Meadows et al. |
| 7,805,189 B2 | 9/2010 | Stein |
| 7,818,068 B2 | 10/2010 | Meadows et al. |
| 7,826,901 B2 | 11/2010 | Lee et al. |
| 7,848,812 B2 | 12/2010 | Crowley et al. |
| 7,856,277 B1 | 12/2010 | Thacker et al. |
| 7,865,245 B2 | 1/2011 | Torgerson et al. |
| 7,879,495 B2 | 2/2011 | Howard et al. |
| 7,894,905 B2 | 2/2011 | Pless et al. |
| 7,941,220 B2 | 5/2011 | Tobacman |
| 7,957,809 B2 | 6/2011 | Bourget et al. |
| 7,991,483 B1 | 8/2011 | Atanasoska |
| 7,996,055 B2 | 8/2011 | Hauck et al. |
| 8,016,776 B2 | 9/2011 | Bourget et al. |
| 8,128,600 B2 | 3/2012 | Gill |
| 8,131,357 B2 | 3/2012 | Bradley et al. |
| 8,150,521 B2 | 4/2012 | Crowley |
| 8,170,675 B2 | 5/2012 | Alataris et al. |
| 8,180,445 B1 | 5/2012 | Moffitt |
| 8,190,259 B1 | 5/2012 | Smith et al. |
| 8,197,494 B2 | 6/2012 | Jaggi et al. |
| 8,209,021 B2 | 6/2012 | Alataris et al. |
| 8,209,028 B2 | 6/2012 | Skelton et al. |
| 8,224,453 B2 | 7/2012 | De Ridder |
| 8,355,791 B2 | 1/2013 | Moffitt |
| 8,355,797 B2 | 1/2013 | Caparso et al. |
| 8,380,318 B2 | 2/2013 | Kishawi et al. |
| 8,423,147 B2 | 4/2013 | Alataris et al. |
| 8,428,748 B2 | 4/2013 | Alataris et al. |
| 8,527,062 B2 | 9/2013 | Dai et al. |
| 8,571,679 B2 | 10/2013 | Parramon et al. |
| 8,583,954 B2 | 11/2013 | Dinsmoor |
| 8,712,534 B2 | 4/2014 | Wei |
| 8,929,986 B2 | 1/2015 | Parker |
| 8,965,514 B2 | 2/2015 | Bikson et al. |
| 9,013,938 B1 | 4/2015 | Moscaluk et al. |

(56) References Cited

U.S. PATENT DOCUMENTS

| | | |
|---|---|---|
| 9,061,152 B2 | 6/2015 | Shi et al. |
| 9,192,769 B2 | 11/2015 | Donofrio et al. |
| 9,227,076 B2 | 1/2016 | Sharma et al. |
| 9,248,293 B2 | 2/2016 | Walker et al. |
| 9,409,020 B2 | 8/2016 | Parker et al. |
| 9,466,997 B2 | 10/2016 | Silva |
| 9,533,164 B2 | 1/2017 | Erickson |
| 9,700,724 B2 | 7/2017 | Liu et al. |
| 9,764,147 B2 | 9/2017 | Togerson |
| 10,173,062 B2 | 1/2019 | Parker |
| 10,207,109 B2 | 2/2019 | Zhu et al. |
| 10,420,935 B2 | 9/2019 | Illegems |
| 10,493,275 B2 | 12/2019 | Alataris et al. |
| 10,537,740 B2 | 1/2020 | Cabunaru |
| 10,881,857 B2 | 1/2021 | Parker |
| 10,946,204 B2 | 3/2021 | Sharma |
| 11,235,153 B2 | 2/2022 | Kibler et al. |
| 2002/0035385 A1 | 3/2002 | Deziz |
| 2002/0068956 A1 | 6/2002 | Bloemer et al. |
| 2002/0107554 A1 | 8/2002 | Biggs et al. |
| 2002/0193844 A1 | 12/2002 | Michelson et al. |
| 2003/0107349 A1 | 6/2003 | Haydock et al. |
| 2003/0110058 A1 | 6/2003 | Adie |
| 2003/0114899 A1 | 6/2003 | Woods et al. |
| 2003/0135241 A1 | 7/2003 | Leonard et al. |
| 2003/0191504 A1 | 10/2003 | Meadows et al. |
| 2003/0195581 A1 | 10/2003 | Meadows et al. |
| 2003/0199952 A1 | 10/2003 | Stolz et al. |
| 2003/0204221 A1 | 10/2003 | Rodriguez et al. |
| 2003/0204222 A1 | 10/2003 | Leinders et al. |
| 2003/0208244 A1 | 11/2003 | Stein et al. |
| 2004/0034393 A1 | 2/2004 | Hansen et al. |
| 2004/0098060 A1 | 5/2004 | Ternes |
| 2004/0176812 A1 | 9/2004 | Knudson et al. |
| 2004/0186544 A1 | 9/2004 | King |
| 2004/0199214 A1 | 10/2004 | Merfeld et al. |
| 2004/0210290 A1 | 10/2004 | Omar-Pasha |
| 2004/0215287 A1 | 10/2004 | Swoyer et al. |
| 2004/0225333 A1 | 11/2004 | Greatbatch |
| 2005/0004417 A1 | 1/2005 | Nelson et al. |
| 2005/0004638 A1 | 1/2005 | Cross |
| 2005/0025480 A1 | 2/2005 | Yeh |
| 2005/0038489 A1 | 2/2005 | Grill |
| 2005/0049664 A1 | 3/2005 | Harris et al. |
| 2005/0075695 A1 | 4/2005 | Schommer et al. |
| 2005/0131483 A1 | 6/2005 | Zhao |
| 2005/0143787 A1 | 6/2005 | Boveja et al. |
| 2005/0174098 A1 | 8/2005 | Watanabe |
| 2005/0178372 A1 | 8/2005 | Kesler et al. |
| 2005/0203583 A1 | 9/2005 | Twetan et al. |
| 2005/0203584 A1 | 9/2005 | Twetan et al. |
| 2005/0218726 A1 | 10/2005 | Jenson |
| 2005/0266301 A1 | 12/2005 | Smith et al. |
| 2005/0267546 A1 | 12/2005 | Parramon et al. |
| 2006/0004422 A1 | 1/2006 | De Ridder |
| 2006/0089697 A1 | 4/2006 | Cross et al. |
| 2006/0122655 A1 | 6/2006 | Greatbatch et al. |
| 2006/0190060 A1 | 8/2006 | Greeninger |
| 2006/0224208 A1 | 10/2006 | Naviaux |
| 2007/0060955 A1 | 3/2007 | Strother et al. |
| 2007/0060968 A1 | 3/2007 | Strother et al. |
| 2007/0060980 A1 | 3/2007 | Strother et al. |
| 2007/0066995 A1 | 3/2007 | Strother et al. |
| 2007/0093875 A1 | 4/2007 | Chavan et al. |
| 2007/0111587 A1 | 5/2007 | Ries et al. |
| 2007/0129768 A1 | 6/2007 | He |
| 2007/0142728 A1 | 6/2007 | Penner |
| 2007/0142874 A1 | 6/2007 | John |
| 2007/0162088 A1 | 7/2007 | Chen et al. |
| 2007/0210759 A1 | 9/2007 | Sano |
| 2007/0265489 A1 | 11/2007 | Fowler et al. |
| 2007/0270916 A1 | 11/2007 | Fischell et al. |
| 2008/0015644 A1 | 1/2008 | Julian |
| 2008/0039904 A1 | 2/2008 | Bulkes et al. |
| 2008/0058901 A1 | 3/2008 | Ternes et al. |
| 2008/0065182 A1 | 3/2008 | Strother et al. |
| 2008/0077184 A1 | 3/2008 | Denker et al. |
| 2008/0097554 A1 | 4/2008 | Payne et al. |
| 2008/0125833 A1 | 5/2008 | Bradley et al. |
| 2008/0129225 A1 | 6/2008 | Yamamoto et al. |
| 2008/0132926 A1 | 6/2008 | Eichmann et al. |
| 2008/0140153 A1 | 6/2008 | Burdulis |
| 2008/0156333 A1 | 7/2008 | Galpern et al. |
| 2008/0216846 A1 | 9/2008 | Levin |
| 2008/0243210 A1 | 10/2008 | Doron |
| 2008/0255631 A1 | 10/2008 | Sjostedt et al. |
| 2008/0262563 A1 | 10/2008 | Sjostedt |
| 2008/0294219 A1 | 11/2008 | Osypka et al. |
| 2008/0319441 A1 | 12/2008 | Seid |
| 2009/0012576 A1 | 1/2009 | Erbstoeszer et al. |
| 2009/0017700 A1 | 1/2009 | Zart et al. |
| 2009/0018600 A1 | 1/2009 | Deininger et al. |
| 2009/0018607 A1 | 1/2009 | Crowley et al. |
| 2009/0048643 A1 | 2/2009 | Erickson |
| 2009/0132010 A1 | 5/2009 | Kronberg |
| 2009/0157138 A1 | 6/2009 | Errico et al. |
| 2009/0157142 A1 | 6/2009 | Cauller |
| 2009/0204119 A1 | 8/2009 | Bleich et al. |
| 2009/0204173 A1 | 8/2009 | Fang |
| 2009/0210029 A1 | 8/2009 | Tsui |
| 2009/0228074 A1 | 9/2009 | Edgell et al. |
| 2009/0248094 A1 | 10/2009 | McDonald |
| 2009/0248118 A1 | 10/2009 | Bradley et al. |
| 2009/0270948 A1 | 10/2009 | Nghiem et al. |
| 2009/0281596 A1 | 11/2009 | King |
| 2009/0281599 A1 | 11/2009 | Thacker et al. |
| 2009/0287946 A1 | 11/2009 | Lin |
| 2010/0004654 A1 | 1/2010 | Schmitz et al. |
| 2010/0010567 A1 | 1/2010 | Deem et al. |
| 2010/0038132 A1 | 2/2010 | Kinney et al. |
| 2010/0049275 A1 | 2/2010 | Chavan et al. |
| 2010/0094115 A1 | 4/2010 | Pond, Jr. et al. |
| 2010/0094231 A1 | 4/2010 | Bleich et al. |
| 2010/0106223 A1 | 4/2010 | Grevious et al. |
| 2010/0137943 A1 | 6/2010 | Zhu |
| 2010/0137944 A1 | 6/2010 | Zhu |
| 2010/0144281 A1 | 6/2010 | Kim et al. |
| 2010/0144283 A1 | 6/2010 | Curcio et al. |
| 2010/0168818 A1 | 7/2010 | Barror et al. |
| 2010/0233896 A1 | 9/2010 | Dilmaghanian |
| 2010/0274312 A1 | 10/2010 | Alataris |
| 2010/0274314 A1 | 10/2010 | Alataris et al. |
| 2010/0274317 A1 | 10/2010 | Parker et al. |
| 2010/0305631 A1 | 12/2010 | Bradley et al. |
| 2010/0305663 A1 | 12/2010 | Aghassian |
| 2010/0324570 A1 | 12/2010 | Rooney et al. |
| 2010/0331920 A1 | 12/2010 | DiGiore et al. |
| 2011/0054583 A1 | 3/2011 | Litt et al. |
| 2011/0060282 A1 | 3/2011 | Dogwiler et al. |
| 2011/0071589 A1 | 3/2011 | Starkebaum et al. |
| 2011/0112601 A1 | 5/2011 | Meadows et al. |
| 2011/0112609 A1 | 5/2011 | Peterson |
| 2011/0112610 A1 | 5/2011 | Rahman et al. |
| 2011/0118661 A1 | 5/2011 | Pless et al. |
| 2011/0144468 A1 | 6/2011 | Boggs et al. |
| 2011/0160804 A1 | 6/2011 | Penner |
| 2011/0184488 A1 | 7/2011 | De Ridder |
| 2011/0224710 A1 | 9/2011 | Bleich |
| 2011/0245708 A1 | 10/2011 | Finkel et al. |
| 2011/0270363 A1 | 11/2011 | Schramm |
| 2011/0301679 A1 | 12/2011 | Rezai |
| 2012/0066534 A1 | 3/2012 | Dinsmoor |
| 2012/0095744 A1 | 4/2012 | Rahman et al. |
| 2012/0101551 A1 | 4/2012 | Aghassian et al. |
| 2012/0239108 A1 | 9/2012 | Foutz |
| 2012/0253440 A1 | 10/2012 | Grohmann |
| 2012/0315798 A1 | 12/2012 | Poon et al. |
| 2013/0035740 A1 | 2/2013 | Sharma et al. |
| 2013/0066399 A1 | 3/2013 | Min |
| 2013/0066411 A1 | 3/2013 | Thacker et al. |
| 2013/0238048 A1 | 9/2013 | Almendinger et al. |
| 2013/0282078 A1 | 10/2013 | Wacnik |
| 2014/0180361 A1 | 1/2014 | Burdick et al. |
| 2014/0067016 A1 | 3/2014 | Kaula |

(56) References Cited

U.S. PATENT DOCUMENTS

| | | |
|---|---|---|
| 2014/0081350 A1 | 3/2014 | Zhu |
| 2014/0121787 A1 | 5/2014 | Yamazaki |
| 2014/0217291 A1 | 8/2014 | Deutscher |
| 2014/0277268 A1 | 9/2014 | Lee |
| 2014/0343622 A1 | 11/2014 | Alataris |
| 2014/0343623 A1 | 11/2014 | Alves et al. |
| 2015/0005842 A1 | 1/2015 | Lee |
| 2015/0039047 A1 | 2/2015 | Parker |
| 2015/0039048 A1 | 2/2015 | Woods |
| 2015/0088227 A1 | 3/2015 | Shishilla et al. |
| 2015/0151125 A1 | 6/2015 | Zhu |
| 2015/0165209 A1 | 6/2015 | Grandhe |
| 2015/0321000 A1 | 11/2015 | Rosenbluth |
| 2016/0114171 A1 | 4/2016 | Parker |
| 2016/0124455 A1 | 5/2016 | Sambucco et al. |
| 2016/0158551 A1 | 6/2016 | Kent |
| 2016/0175586 A1 | 6/2016 | Edgerton et al. |
| 2016/0256696 A1 | 9/2016 | Sharma et al. |
| 2016/0271392 A1 | 9/2016 | Vallejo et al. |
| 2017/0189686 A1 | 7/2017 | Steinke et al. |
| 2017/0202607 A1 | 7/2017 | Shelton |
| 2018/0256892 A1 | 9/2018 | Wong |
| 2018/0345022 A1 | 12/2018 | Steinke et al. |
| 2019/0022382 A1 | 1/2019 | Gerasimenko et al. |
| 2019/0232064 A1 | 8/2019 | Parker |
| 2019/0341803 A1 | 11/2019 | Cook |
| 2021/0335285 A1 | 10/2021 | Liu |

FOREIGN PATENT DOCUMENTS

| | | |
|---|---|---|
| EP | 2243510 | 10/2010 |
| EP | 2586491 | 8/2016 |
| JP | 2002090196 | 3/2002 |
| WO | WO-20080121110 | 10/2008 |
| WO | WO-2011094074 A1 | 8/2011 |
| WO | WO-2012054234 | 4/2012 |
| WO | WO-2020236946 | 11/2020 |

OTHER PUBLICATIONS

North et al., "Spinal Cord Stimulation for Chronic, Intractable Pain: Experience over Two Decades," Neurosurgery, vol. 32, No. 2, Mar. 1993, 12 pages.

Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.

International Search Report and Written Opinion for International Patent Application No. PCT/US2015/030402, Applicant: Nevro Corporation, dated Sep. 17, 2015, 8 pages.

European Extended Search Report (EPSR) for European Patent Application No. 15795695.4, Applicant: Nevro Corporation, dated Sep. 26, 2017, 9 pages.

European Extended Search Report for European Patent Application No. 20202407.1, Applicant: Nevro Corporation, dated Jul. 27, 2021, 10 pages.

Cappaert et al., "Efficacy of a New Charge-Balanced Biphasic Electrical Stimulus in the Isolated Sciatic Nerve and the Hippocampal Slice," International Journal of Neural Systems, vol. 23, No. 1, 2013, 16 pages.

Hofmann et al., "Modified Pulse Shapes for Effective Neural Stimulation," Frontiers in Neuroengineering, Sep. 28, 2011, 10 pages.

\* cited by examiner

IMPLANTED PULSE GENERATORS WITH REDUCED POWER CONSUMPTION VIA SIGNAL STRENGTH/DURATION CHARACTERISTICS, AND ASSOCIATED SYSTEMS AND METHODS

CROSS-REFERENCE TO RELATED APPLICATION

The present application is a continuation of U.S. patent application Ser. No. 16/183,456, filed Nov. 7, 2018, which is a continuation of U.S. patent application Ser. No. 15/227,821, now issued as U.S. Pat. No. 10,176,062, file Aug. 3, 2016, which is a continuation of U.S. patent application Ser. No. 14/710,375, now issued as U.S. Pat. No. 9,409,020, filed May 12, 2015, which claims priority to U.S. Provisional Application 62/000,985, filed on May 20, 2014, each of which are incorporated herein by reference.

TECHNICAL FIELD

The present technology is directed generally to implanted pulse generators with reduced power consumption, obtained via signal strength/duration characteristics, and associated systems and methods. Particular embodiments use a strength/duration characteristics to improve the delivery of electrical stimulation for patient therapy, as the voltage available from an implanted power source decreases.

BACKGROUND

Neurological stimulators have been developed to treat pain, movement disorders, functional disorders, spasticity, cancer, cardiac disorders, and various other medical conditions. Implantable neurological stimulation systems generally have an implantable signal generator and one or more leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings (i.e., contacts) spaced apart from each other at the distal end of the lead body. The conductive rings operate as individual electrodes and, in many cases, the SCS leads are implanted percutaneously through a needle inserted into the epidural space, with or without the assistance of a stylet.

Once implanted, the signal generator applies electrical pulses to the electrodes, which in turn modify the function of the patient's nervous system, such as by altering the patient's responsiveness to sensory stimuli and/or altering the patient's motor-circuit output. In SCS therapy for the treatment of pain, the signal generator applies electrical pulses to the spinal cord via the electrodes. In conventional SCS therapy, electrical pulses are used to generate sensations (known as paresthesia) that mask or otherwise alter the patient's sensation of pain. For example, in many cases, patients report paresthesia as a tingling sensation that is perceived as less uncomfortable than the underlying pain sensation.

In contrast to traditional or conventional (i.e., paresthesia-based) SCS, a form of paresthesia-free SCS has been developed that uses therapy signal parameters that treat the patient's sensation of pain without generating paresthesia or otherwise using paresthesia to mask the patient's sensation of pain. One of several advantages of paresthesia-free SCS therapy systems is that they eliminate the need for uncomfortable paresthesias, which many patients find objectionable. However, a challenge with paresthesia-free SCS therapy systems is that the signal may be delivered at frequencies, amplitudes, and/or pulse widths that may use more power than conventional SCS systems. This in turn can deplete the battery of the implanted system at an accelerated rate. Accordingly, a follow-on challenge with providing spinal cord stimulation via an implanted pulse generator is that, in at least some cases, it may be difficult to maintain an effective signal as the charge available from the pulse generator battery decreases. One approach to the challenge in the context of conventional systems is to increase the frequency with which the pulse generator is charged, but this can be inconvenient for the patient. Another approach is to add signal conditioning hardware, for example, to boost the voltage provided by the battery as the battery discharges. A drawback with this approach is that it can be inefficient. Accordingly, there remains a need for effective and efficient therapy signal delivery, despite the decreasing voltage available from the battery or other power source of an implanted pulse generator during normal use.

DETAILED DESCRIPTION

Figure 1A:
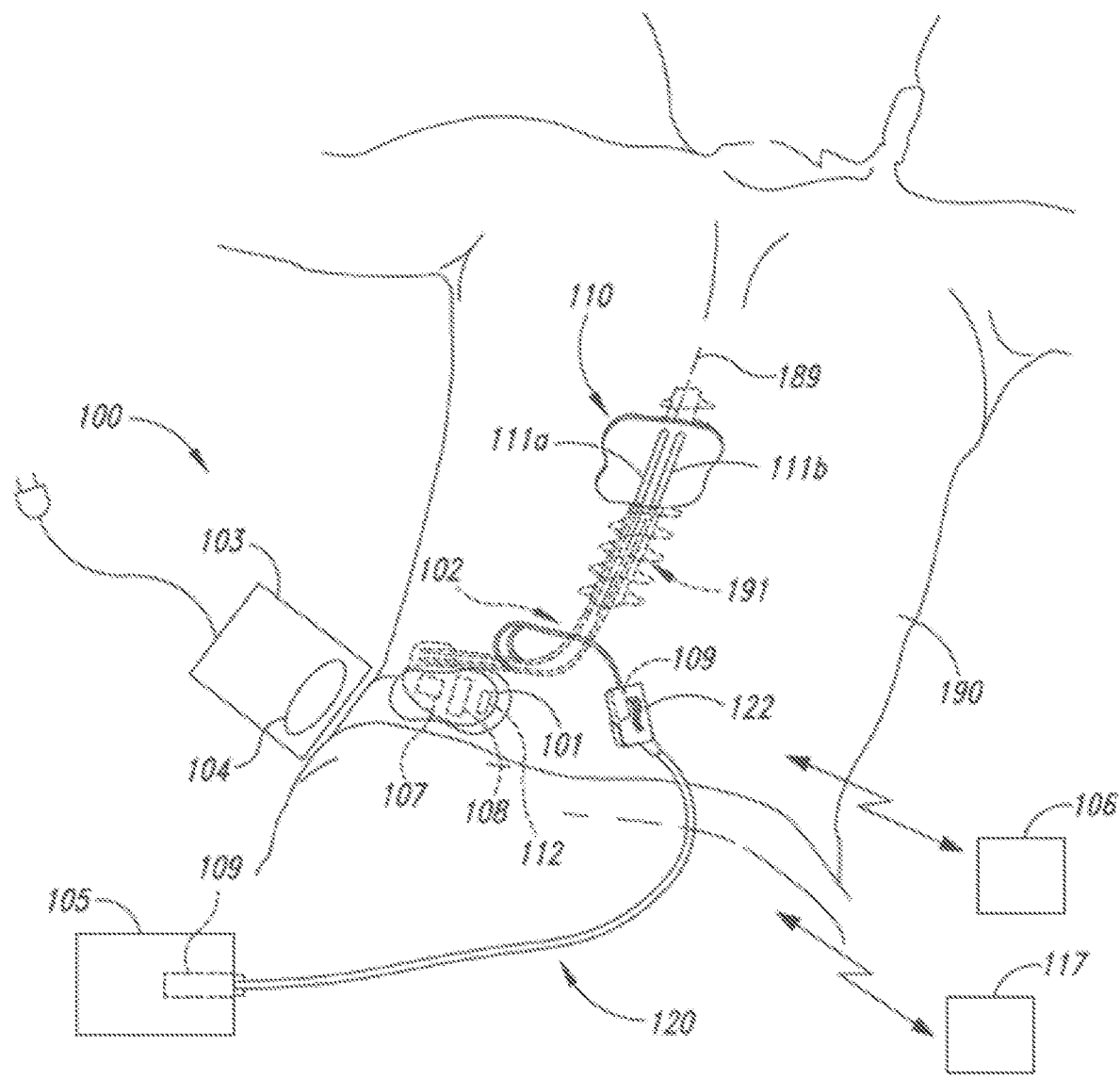
FIG. 1A is a partially schematic illustration of an implantable spinal cord modulation system positioned at the spine to deliver therapeutic signals in accordance with several embodiments of the present technology.

The present technology is directed generally to delivering electrical signals (also referred to herein as "therapy signals") at reduced available voltage levels in implanted patient therapy systems, such as spinal cord stimulation (SCS) systems. For example, in one embodiment, the present technology includes reducing signal amplitude and increasing pulse width or duty cycle to maintain a target energy delivery rate. Because the technology can be employed in SCS systems that provide therapy (e.g., pain relief) without generating paresthesia, the patient can continue to receive effective therapy without sensing the amplitude change. Accordingly, the present technology can effectively increase the time between battery charging events, thus addressing potential instances in which paresthesia-free therapy might otherwise deplete the power available from an implanted battery faster than would a conventional, paresthesia-based device.

General aspects of the environments in which the disclosed technology operates are described below under heading 1.0 ("Overview") with reference to FIGS. 1A and 1B. Particular embodiments of the technology are described further under heading 2.0 ("Representative Embodiments") with reference to FIGS. 2-6. While the present technology is being described in the environment of SCS, one of skill in the art would recognize that one or more aspects of the present technology are applicable to other, non-SCS implantable and/or external devices; e.g., implantable or external neurostimulators for treatment of one or more patient indications.

1.0 OVERVIEW

One example of a paresthesia-free SCS therapy system is a "high frequency" SCS system. High frequency SCS systems can inhibit, reduce, and/or eliminate pain via waveforms with high frequency elements or components (e.g., portions having high fundamental frequencies), generally with reduced or eliminated side effects. Such side effects can include unwanted paresthesia, unwanted motor stimulation or blocking, unwanted pain or discomfort, and/or interference with sensory functions other than the targeted pain. In a representative embodiment, a patient may receive high frequency therapeutic signals with at least a portion of the therapy signal at a frequency of from about 1.5 kHz to about 100 kHz, or from about 1.5 kHz to about 50 kHz, or from about 3 kHz to about 20 kHz, or from about 5 kHz to about 15 kHz, or at frequencies of about 8 kHz, 9 kHz, or 10 kHz. These frequencies are significantly higher than the frequencies associated with conventional "low frequency" SCS, which are generally below 1,200 Hz, and more commonly below 100 Hz. Accordingly, modulation at these and other representative frequencies (e.g., from about 1.5 kHz to about 100 kHz) is occasionally referred to herein as "high frequency stimulation," "high frequency SCS," and/or "high frequency modulation." Further examples of paresthesia-free SCS systems are described in U.S. Patent Publication Nos. 2009/0204173 and 2010/0274314, as well as U.S. Provisional Application No. 61/901,255, the respective disclosures of which are herein incorporated by reference in their entirety.

FIG. 1A schematically illustrates a representative patient therapy system 100 for providing relief from chronic pain and/or other conditions, arranged relative to the general anatomy of a patient's spinal column 191. The system 100 can include a signal generator 101 (e.g., an implanted pulse generator or IPG), which may be implanted subcutaneously within a patient 190 and coupled to one or more signal delivery elements or devices 110. The signal delivery elements or devices 110 may be implanted within the patient 190, typically at or near the patient's spinal cord midline 189. The signal delivery elements 110 carry features for delivering therapy to the patient 190 after implantation. The signal generator 101 can be connected directly to the signal delivery devices 110, or it can be coupled to the signal delivery devices 110 via a signal link or lead extension 102. In a further representative embodiment, the signal delivery devices 110 can include one or more elongated lead(s) or lead body or bodies 111 (identified individually as a first lead 111a and a second lead 111b). As used herein, the terms signal delivery device, lead, and/or lead body include any of a number of suitable substrates and/or support members that carry electrodes/devices for providing therapy signals to the patient 190. For example, the lead or leads 111 can include one or more electrodes or electrical contacts that direct electrical signals into the patient's tissue, e.g., to provide for therapeutic relief. In other embodiments, the signal delivery elements 110 can include structures other than a lead body (e.g., a paddle) that also direct electrical signals and/or other types of signals to the patient 190.

In a representative embodiment, one signal delivery device may be implanted on one side of the spinal cord midline 189, and a second signal delivery device may be implanted on the other side of the spinal cord midline 189. For example, the first and second leads 111a, 111b shown in FIG. 1A may be positioned just off the spinal cord midline 189 (e.g., about 1 mm offset) in opposing lateral directions so that the two leads 111a, 111b are spaced apart from each other by about 2 mm. In particular embodiments, the leads 111 may be implanted at a vertebral level ranging from, for example, about T8 to about T12. In other embodiments, one or more signal delivery devices can be implanted at other vertebral levels, e.g., as disclosed in U.S. Patent Application Publication No. 2013/0066411, and incorporated herein by reference in its entirety.

The signal generator 101 can transmit signals (e.g., electrical signals) to the signal delivery elements 110 that up-regulate (e.g., excite) and/or down-regulate (e.g., block or suppress) target nerves. As used herein, and unless otherwise noted, the terms "modulate," "modulation," "stimulate," and "stimulation" refer generally to signals that have either type of the foregoing effects on the target nerves. The signal generator 101 can include a machine-readable (e.g., computer-readable) medium containing instructions for generating and transmitting suitable therapy signals. The signal generator 101 and/or other elements of the system 100 can include one or more processor(s) 107, memory unit(s) 108, and/or input/output device(s) 112. Accordingly, the process of providing modulation signals, providing guidance information for positioning the signal delivery devices 110, and/or executing other associated functions can be performed by computer-executable instructions contained by, on or in computer-readable media located at the pulse generator 101 and/or other system components. Further, the pulse generator 101 and/or other system components may include dedicated hardware, firmware, and/or software for executing computer-executable instructions that, when executed, perform any one or more methods, processes, and/or sub-processes described herein; e.g., the methods, processes, and/or sub-processes described with reference to FIGS. 2-6 below. Said dedicated hardware, firmware, and/or software also serve as "means for" performing the methods, processes, and/or sub-processes described herein. The signal generator 101 can also include multiple portions, elements, and/or subsystems (e.g., for directing signals in accordance with multiple signal delivery parameters), carried in a single housing, as shown in FIG. 1A, or in multiple housings.

The signal generator 101 can also receive and respond to an input signal received from one or more sources. The input signals can direct or influence the manner in which the therapy and/or process instructions are selected, executed, updated, and/or otherwise performed. The input signals can be received from one or more sensors (e.g., an input device 112 shown schematically in FIG. 1 for purposes of illustration) that are carried by the signal generator 101 and/or distributed outside the signal generator 101 (e.g., at other patient locations) while still communicating with the signal generator 101. The sensors and/or other input devices 112 can provide inputs that depend on or reflect patient state (e.g., patient position, patient posture, and/or patient activity level), and/or inputs that are patient-independent (e.g., time).

Still further details are included in U.S. Pat. No. 8,355,797, incorporated herein by reference in its entirety.

In some embodiments, the signal generator 101 and/or signal delivery devices 110 can obtain power to generate the therapy signals from an external power source 103. In one embodiment, for example, the external power source 103 can by-pass an implanted signal generator and generate a therapy signal directly at the signal delivery devices 110 (or via signal relay components). The external power source 103 can transmit power to the implanted signal generator 101 and/or directly to the signal delivery devices 110 using electromagnetic induction (e.g., RF signals). For example, the external power source 103 can include an external coil 104 that communicates with a corresponding internal coil (not shown) within the implantable signal generator 101, signal delivery devices 110, and/or a power relay component (not shown). The external power source 103 can be portable for ease of use.

In another embodiment, the signal generator 101 can obtain the power to generate therapy signals from an internal power source, in addition to or in lieu of the external power source 103. For example, the implanted signal generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

During at least some procedures, an external stimulator or trial modulator 105 can be coupled to the signal delivery elements 110 during an initial procedure, prior to implanting the signal generator 101. For example, a practitioner (e.g., a physician and/or a company representative) can use the trial modulator 105 to vary the modulation parameters provided to the signal delivery elements 110 in real time, and select optimal or particularly efficacious parameters. These parameters can include the location from which the electrical signals are emitted, as well as the characteristics of the electrical signals provided to the signal delivery devices 110. In some embodiments, input is collected via the external stimulator or trial modulator and can be used by the clinician to help determine what parameters to vary. In a typical process, the practitioner uses a cable assembly 120 to temporarily connect the trial modulator 105 to the signal delivery device 110. The practitioner can test the efficacy of the signal delivery devices 110 in an initial position. The practitioner can then disconnect the cable assembly 120 (e.g., at a connector 122), reposition the signal delivery devices 110, and reapply the electrical signals. This process can be performed iteratively until the practitioner obtains the desired position for the signal delivery devices 110. Optionally, the practitioner may move the partially implanted signal delivery devices 110 without disconnecting the cable assembly 120. Furthermore, in some embodiments, the iterative process of repositioning the signal delivery devices 110 and/or varying the therapy parameters may not be performed.

The signal generator 101, the lead extension 102, the trial modulator 105 and/or the connector 122 can each include a receiving element 109. Accordingly, the receiving elements 109 can be patient implantable elements, or the receiving elements 109 can be integral with an external patient treatment element, device or component (e.g., the trial modulator 105 and/or the connector 122). The receiving elements 109 can be configured to facilitate a simple coupling and decoupling procedure between the signal delivery devices 110, the lead extension 102, the pulse generator 101, the trial modulator 105 and/or the connector 122. The receiving elements 109 can be at least generally similar in structure and function to those described in U.S. Patent Application Publication No. 2011/0071593, incorporated by reference herein in its entirety.

After the signal delivery elements 110 are implanted, the patient 190 can receive therapy via signals generated by the trial modulator 105, generally for a limited period of time. During this time, the patient wears the cable assembly 120 and the trial modulator 105 outside the body. Assuming the trial therapy is effective or shows the promise of being effective, the practitioner then replaces the trial modulator 105 with the implanted signal generator 101, and programs the signal generator 101 with therapy programs selected based on the experience gained during the trial period. Optionally, the practitioner can also replace the signal delivery elements 110. Once the implantable signal generator 101 has been positioned within the patient 190, the therapy programs provided by the signal generator 101 can still be updated remotely via a wireless physician's programmer (e.g., a physician's laptop, a physician's remote or remote device, etc.) 117 and/or a wireless patient programmer 106 (e.g., a patient's laptop, patient's remote or remote device, etc.). Generally, the patient 190 has control over fewer parameters than does the practitioner. For example, the capability of the patient programmer 106 may be limited to starting and/or stopping the signal generator 101, and/or adjusting the signal amplitude. The patient programmer 106 may be configured to accept pain relief input as well as other variables, such as medication use.

In any of the foregoing embodiments, the parameters in accordance with which the signal generator 101 provides signals can be adjusted during portions of the therapy regimen. For example, the frequency, amplitude, pulse width, and/or signal delivery location can be adjusted in accordance with a pre-set therapy program, patient and/or physician inputs, and/or in a random or pseudorandom manner. Such parameter variations can be used to address a number of potential clinical situations. Certain aspects of the foregoing systems and methods may be simplified or eliminated in particular embodiments of the present disclosure. Further aspects of these and other expected beneficial results are detailed in U.S. Patent Application Publication Nos. 2010/0274317; 2010/0274314; 2009/0204173; and 2013/0066411, each of which is incorporated herein by reference in its entirety.

Figure 1B:
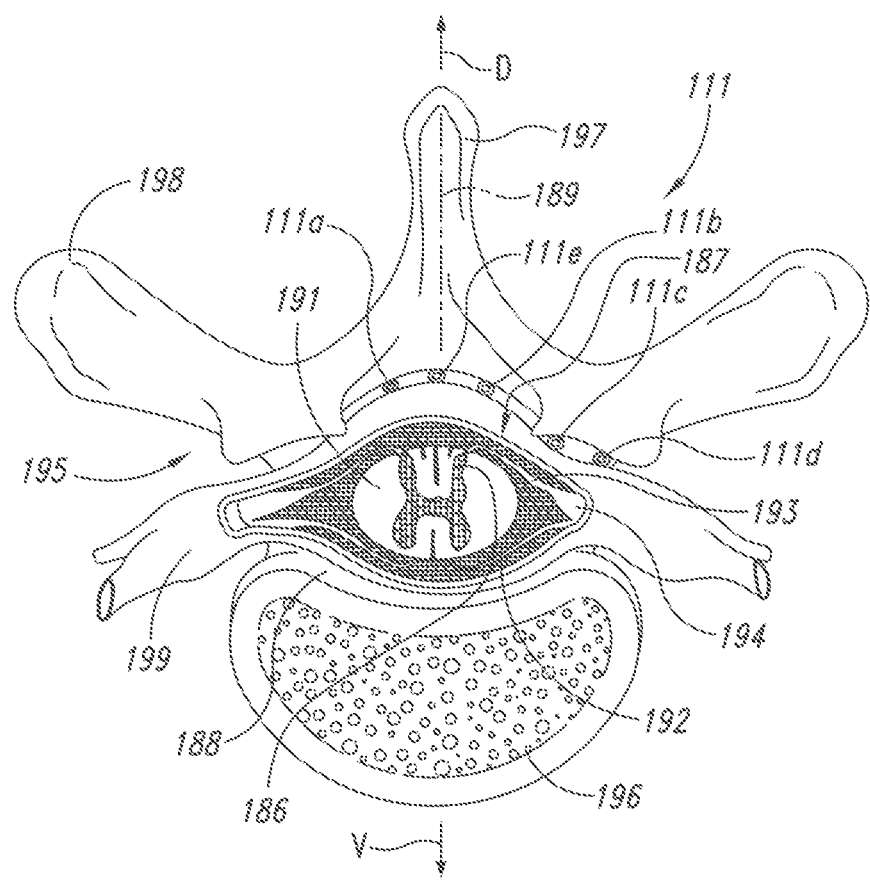
FIG. 1B is a partially schematic, cross-sectional illustration of a patient's spine, illustrating representative locations for implanted lead bodies in accordance with embodiments of the present technology.

FIG. 1B is a cross-sectional illustration of the spinal cord 191 and an adjacent vertebra 195 (based generally on information from Crossman and Neary, "Neuroanatomy," 1995 (published by Churchill Livingstone)), along with multiple leads 111 (shown as leads 111a-111e) implanted at representative locations. For purposes of illustration, multiple leads 111 are shown in FIG. 1B implanted in a single patient. In actual use, any given patient will likely receive fewer than all the leads 111 shown in FIG. 1B.

The spinal cord 191 is situated within a vertebral foramen 188, between a ventrally located ventral body 196 and a dorsally located transverse process 198 and spinous process 197. Arrows V and D identify the ventral and dorsal directions, respectively. The spinal cord 191 itself is located within the dura mater 199, which also surrounds portions of the nerves exiting the spinal cord 191, including the ventral roots 192, dorsal roots 193 and dorsal root ganglia 194. The dorsal roots 193 enter the spinal cord 191 at the dorsal root entry zone 187, and communicate with dorsal horn neurons located at the dorsal horn 186. In one embodiment, the first and second leads 111a, 111b are positioned just off the spinal cord midline 189 (e.g., about 1 mm. offset) in opposing lateral directions so that the two leads 111a, 111b are spaced apart from each other by about 2 mm, as discussed above. In other embodiments, a lead or pairs of leads can be positioned at other locations, e.g., toward the outer edge of the dorsal root entry zone 187 as shown by a third lead 111c, or at the dorsal root ganglia 194, as shown by a fourth lead 111d, or approximately at the spinal cord midline 189, as shown by a fifth lead 111e.

2.0 REPRESENTATIVE EMBODIMENTS

As discussed above, systems of the type described with reference to FIGS. 1A-B can include implanted pulse generators having rechargeable batteries or other rechargeable power sources that are periodically recharged with an external recharger. As the battery discharges, the voltage put out by the battery typically also decreases. Conventional techniques for addressing this voltage reduction (and voltage variation generally) include "boost and buck" devices. However, a drawback with such devices is that they are inefficient. In particular, such devices can reduce the overall efficiency of delivering electrical signals to the patient by 20%-30%.

Figure 2:
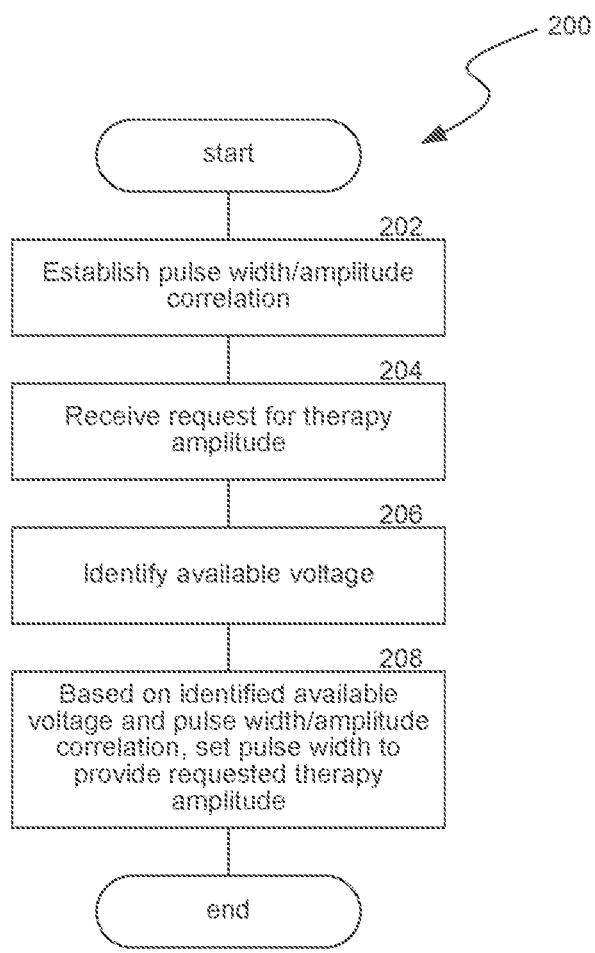
FIG. 2 is a flow diagram illustrating a process for delivering a therapeutic electrical signal in accordance with a representative embodiment of the present technology.

FIG. 2 illustrates a process 200 for more efficiently providing power from an implanted battery (or other power source), as the battery discharges. The process can make use of the relationship between the pulse width and amplitude for therapy signals applied to a patient. Accordingly, the process 200 can include establishing a pulse width/amplitude correlation, e.g., on a patient-by-patient basis (block 202). The process 200 can further include receiving a request for a therapy amplitude (block 204). The request may come via a patient or practitioner selecting a particular therapy program, and/or requesting an amplitude adjustment once the particular program has been activated. The amplitude can be a current amplitude (e.g., in the context of a system that includes a current source between the power source and the electrodes), or a voltage amplitude. In block 206, the available voltage is measured or otherwise identified (e.g., at the battery, or downstream from the battery). The method further includes setting the pulse width to provide the requested therapy amplitude based on the available voltage and the pulse width/amplitude correlation (block 208). Accordingly, the pulse width can be adjusted to provide the same or approximately the same level of therapy to the patient despite the fact that the available voltage (e.g., the battery output voltage) has decreased.

Figure 3:
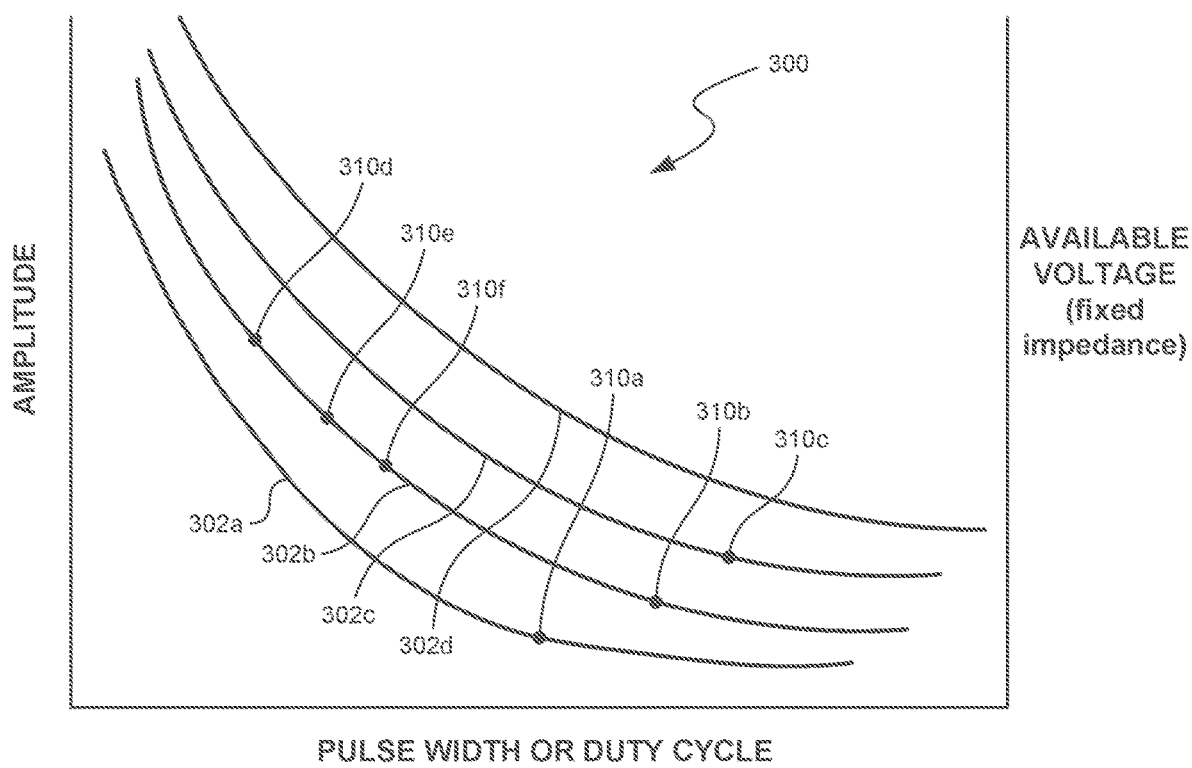
FIG. 3 is a graph illustrating a family of curves representing signal amplitude as a function of pulse width or duty cycle.

FIG. 3 illustrates a graph 300 of signal amplitude as a function of pulse width or duty cycle. For much of the discussion that follows, the functions will be described in the context of amplitude as a function of pulse width, with the understanding that the function and the relationships associated with the function may apply to duty cycle as well.

FIG. 3 illustrates a plurality of curves 302 (four are shown as first-fourth curves 302a-302d) that indicate the functional relationship between amplitude and pulse width for a variety of different patients, evaluation criteria, and/or other factors. These curves are often referred to as "strength-duration" curves. Each curve 302 represents amplitude as a function of pulse width for an effective or target level of electrical stimulation. For example, an effective level of stimulation can include a level of stimulation that provides pain relief without paresthesia. In another embodiment, a target level of stimulation can include stimulation sufficient to generate a sensory response (e.g., paresthesia or another sensation) in the patient. For a given patient, the curve may differ depending upon whether the target result is paresthesia-free therapy, or a sensory response. In addition, the curve for an effective or target stimulation level may be different for one patient than for another. Accordingly, there can exist multiple curves (as shown in FIG. 3) that may be patient-specific and/or target level-specific.

As is also shown in FIG. 3, the pulse width or duty cycle can vary as a function of the available voltage, in a manner similar to the manner in which these parameters vary with amplitude. In particular, each curve 302 can indicate the pulse width or duty cycle appropriate for a given available voltage, assuming a fixed impedance for the signal delivery circuit. Accordingly, FIG. 3 indicates that a given therapy level or efficacy can be delivered with a relatively high voltage and short pulse width, or with a lower voltage and longer pulse width. The relationships between amplitude, available voltage, and pulse width or duty cycle shown in FIG. 3 are used to implement the methods discussed further below with reference to FIGS. 4-6.

Figure 4:
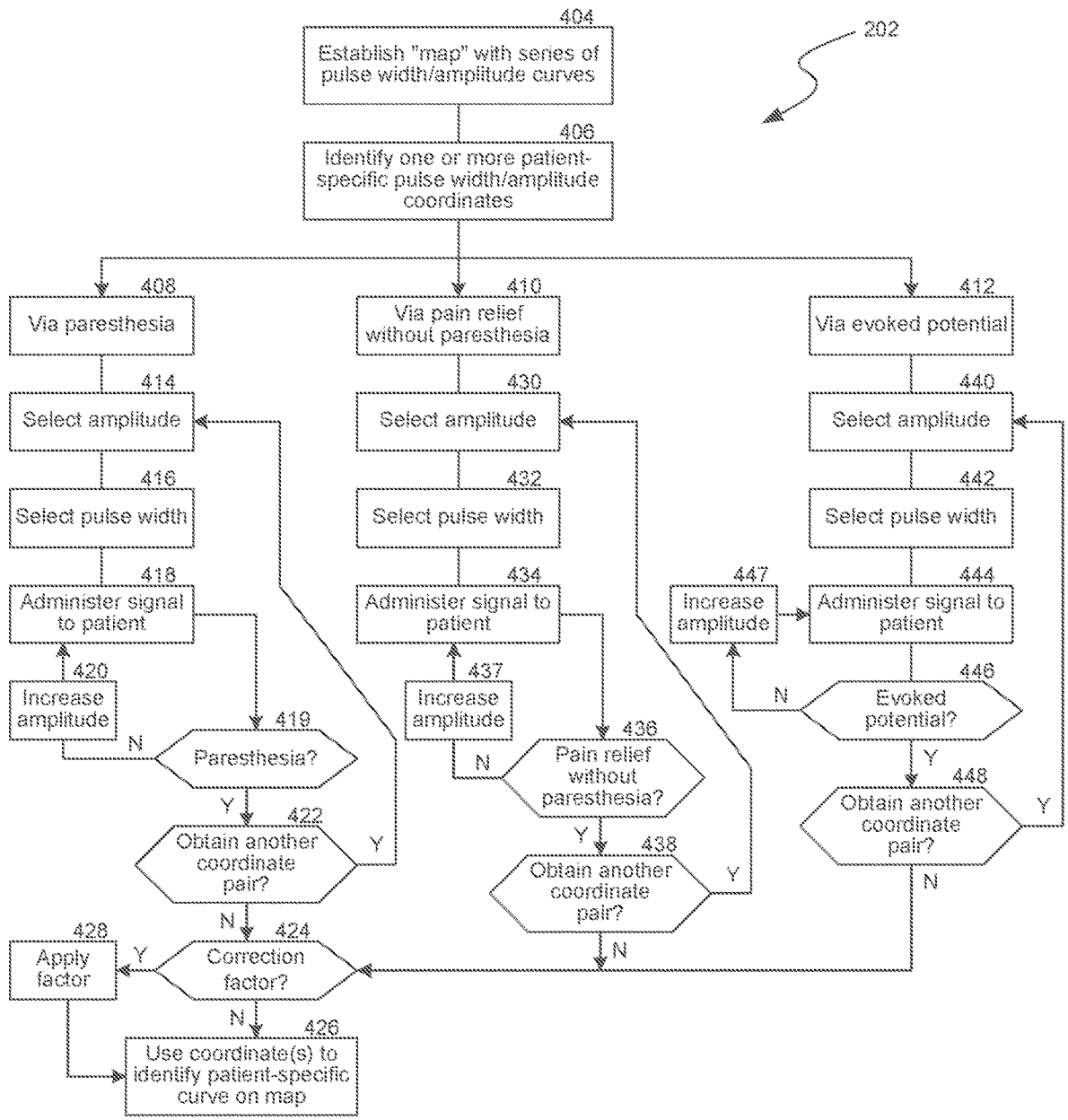
FIG. 4 is a flow diagram illustrating a process for establishing a pulse width/amplitude correlation in accordance with an embodiment of the present technology.

FIG. 4 illustrates representative processes for establishing an amplitude/pulse width correlation, as described above with reference to block 202 in FIG. 2. The process 202 can include establishing a "map" with a series of pulse width/amplitude curves (block 404). The map can have the format shown in FIG. 3 in some embodiments, and in other embodiments, the map can have other formats. Such formats can include other graphical formats, a tabular format, a series of equations describing individual curves or functions, and/or other suitable techniques for establishing a correlation between amplitude and pulse width. The map can be based on clinical data obtained from multiple patients. In particular embodiments, different maps can be established for different parameters (e.g., different patient indications, patient physiologies and/or treatment parameters).

In block 406, the process includes identifying the values (e.g., numerical values) for one or more patient-specific pulse width/amplitude pairs or coordinates. For example, referring to FIG. 3, the practitioner can identify a single point 310a based on data received from the patient, which is sufficient to indicate that the appropriate patient-specific curve is the first curve 302a. The data may indicate that the patient receives effective therapy at the amplitude and pulse width coordinates of the first point 310a. Another patient may be characterized by a second point 310b and accordingly have the second curve 302b as his/her patient-specific curve. Still another patient may be characterized by a third point 310c and accordingly have the third curve 302c as his/her patient-specific curve.

In another embodiment, an individual patient may have a plurality of points associated with him or her, e.g., first-sixth points 310a-310f. In this particular instance, four of the six points (points 310b, 310d, 310e, 310f) fall on the second curve 302b, which can be a sufficient indication that the particular patient's patient-specific curve is the second curve 302b.

In still further embodiments, different points can correspond to a different parameter for the same individual patient. For example, the first point 310a (and the associated first curve 302a) can correspond to a level of paresthesia-free therapy at a particular vertebral level. The second point 310b (and the associated second curve 302b) can correspond to a stimulation threshold, for example, the threshold at which the patient first feels paresthesia or another sensation. The third point 310c (and the associated third curve 302c) can correspond to the threshold at which a signal applied to the patient produces an evoked potential. The evoked potential can be physically measured, thus indicating at which amplitude and pulse width the patient's neurons generate an action potential in response to a stimulus at the amplitude/pulse width coordinates of the third point 310c. Methods for establishing which of the curves shown in FIG. 3 is an appropriate patient-specific curve are further described below, with reference to the three thresholds described above: the paresthesia or sensory threshold, the therapeutic threshold, and the evoked potential threshold.

Returning to FIG. 4, in block 408, the process includes identifying the patient-specific correlation using paresthesia. This process can include selecting an amplitude (block 414), selecting a pulse width (block 416), and administering a signal to the patient in accordance with the selected amplitude and pulse width (block 418). In at least some instances, the pulse width and/or amplitude used for this process may be deliberately selected to be different than the expected pulse width and/or amplitude used for therapy. In particular, the selected amplitude and/or pulse width can be more likely to produce paresthesia. Block 419 includes determining whether the patient reports paresthesia or another suitable sensory feedback. If not, the amplitude is increased at block 420 and the signal is re-administered. Once the patient reports paresthesia, block 422 includes determining whether another coordinate pair (e.g., another pair of amplitude and pulse width values) is to be obtained. If so, the process returns to block 414. If not, the process proceeds to block 424 where it is determined whether or not to apply a correction factor to the coordinate pair or pairs obtained in block 422.

The correction factor can be based on any of a number of suitable parameters. For example, a representative correction factor can include reducing the reported amplitude to account for the expected amplitude difference between a signal that produces paresthesia and a signal that can produce therapy (e.g., pain relief) without paresthesia. If the pulse width used to generate paresthesia is different than the expected therapeutic pulse width, the correction factor can also account for that difference. In any of these embodiments, the correction factor can be patient-specific, or it can be determined from a pool of patient data. The correction factor can be determined empirically through patient testing, or it can be estimated and/or calculated, depending upon the particular embodiment. If such a correction factor is to be applied, it is applied in block 428.

The process then proceeds to block 426 where the coordinate or coordinates, with or without a correction factor, are used to identify the patient-specific curve on the map established at block 404. For example, with reference again to FIG. 3, the coordinates can be used to determine which of the multiple curves 302 best corresponds to or fits with the coordinate or coordinates obtained in block 422. Once the appropriate curve is identified, the curve can be used to select therapeutic amplitudes and pulse widths as a function of available voltage, in a manner described later with reference to FIGS. 5 and 6.

As noted above, block 408 includes identifying the patient-specific curve (or other correlation) in conjunction with a paresthesia threshold identified by the patient. Other techniques can be used to establish which correlation is best suited to an individual patient. For example, block 410 includes identifying the patient-specific correlation based on the threshold at which the patient receives or experiences paresthesia-free pain relief. In this process, the amplitude and pulse width are selected (blocks 430 and 432) and the signal is administered to the patient (block 434). Instead of identifying whether or not the patient has paresthesia, as discussed above with reference to block 419, block 436 can include determining whether the patient has received therapy (e.g., pain relief) without paresthesia. If not, the amplitude is increased in block 437 and the signal is re-administered to the patient. If therapy without paresthesia is obtained, block 438 includes determining whether to obtain an additional coordinate pair. If not, the process proceeds to block 424 to determine whether a correction factor is to be applied and, with or without the correction factor, block 426 includes identifying the patient-specific curve or correlation using the map established in block 404.

In at least some embodiments, it is expected that it may take some time for the patient to detect and report the paresthesia-free therapy (e.g., pain relief). In such instances, it may be more efficient to use the paresthesia threshold technique described above with reference to blocks 408-422 (e.g., with a correction factor applied), or to use other techniques that can more rapidly identify the amplitude/pulse width coordinates. One such technique includes identifying the patient-specific curve or correlation via an evoked potential (block 412). This process also includes selecting an amplitude (block 440), selecting a pulse width (block 442), and applying a therapy signal with the selected amplitude and pulse width (block 444). In block 446, the process includes checking for an evoked potential (e.g., a physiological electrical response to a stimulation signal at the selected amplitude and pulse width). If no evoked potential is measured, then in block 447 the amplitude is increased and the signal is re-administered to the patient in block 444. If an evoked potential is measured, then block 448 includes determining whether or not to obtain an additional amplitude/pulse width coordinate pair. The process then proceeds to block 424 (determining whether or not to apply a correction factor) and to block 426 to identify the patient-specific correlation or curve on the map established in block 404.

Figure 5:
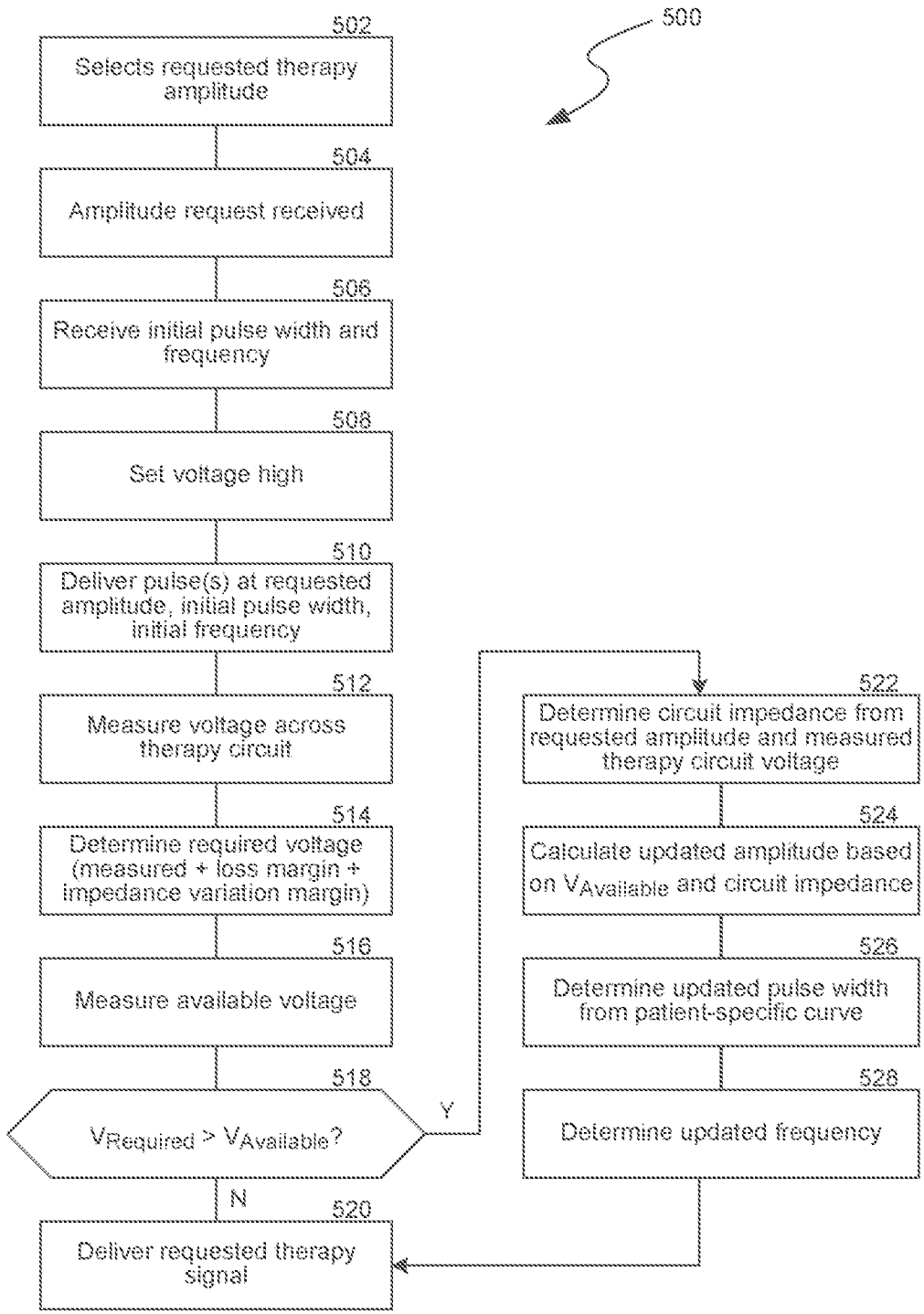
FIG. 5 is a flow diagram illustrating a process for delivering a therapy signal with a reduced available power source voltage in accordance with an embodiment of the present technology.

The result of any of the foregoing embodiments described above with reference FIG. 4 is identifying a patient-specific curve or correlation between signal amplitude and pulse width (or duty cycle). FIG. 5 illustrates a representative process 500 for using this information to identify a therapeutic amplitude and pulse width as a function of a variable available voltage (e.g., battery output voltage or a downstream correlate of battery output voltage). In block 502, the patient or practitioner selects a requested therapy amplitude, which is received by the system at block 504. In block 506, the system receives an initial pulse width and frequency. In at least some embodiments, the initial pulse width and frequency are established by default values stored in memory so that neither the patient nor the practitioner needs to separately input these values. In other embodiments, one or both of these values can be selected by the patient or practitioner. In any of these embodiments, block 508 includes temporarily setting the available voltage high enough to generate a signal at any selected amplitude (within a proscribed limit). This may include using a boost circuit if the battery voltage is insufficient. However, even if a boost circuit is used for this portion of the process, it need not be used to generate the therapy signal over a long period of time, which, as discussed above can reduce system efficiencies.

In block 510, one or more pulses are delivered at the requested amplitude, with the initial pulse width and the initial frequency. As the pulses are delivered, the voltage across the therapy circuit is measured or otherwise determined (block 512). For example, if the signal is delivered to a bipole (two electrodes), the voltage across the bipole is measured. In block 514, the voltage required to deliver a consistent therapy signal at the requested amplitude, and with the initial pulse width and frequency, is determined. This process can include adding a margin (e.g., a loss margin and/or an impedance variation margin) to the therapy circuit voltage measured at block 512. Typical margins range from 100 mV to 1.5V. Accordingly, block 514 can account for one or more system losses, variations, and/or measurement inaccuracies. In block 516, the available voltage is measured. The available voltage can be determined (e.g., measured) at the battery or at any other suitable point (e.g., downstream point) at which the voltage is at least correlated with the available battery voltage. In block 518, the required voltage is compared to the available voltage. If the required voltage does not exceed the available voltage, then the requested therapy signal is delivered at block 520. If the required voltage exceeds the available voltage, then the process continues at block 522.

In block 522, the process includes determining the circuit impedance (e.g., the impedance of the circuit that provides therapy to the patient, including the signal delivery electrodes and the patient's own tissue). The impedance can be obtained using voltage/current/impedance relationships (e.g., V=IR) based on the requested current amplitude (from block 504) and the measured therapy circuit voltage (from block 512). In block 524, the process includes calculating an updated current amplitude based on the available voltage and circuit impedance. Blocks 522 and 524 are typically implemented for a current-based system, e.g., a system with a current source connected between the battery or other power source and the electrodes. Accordingly, these blocks may be skipped or deleted in a voltage-amplitude-based system.

Figure 6:
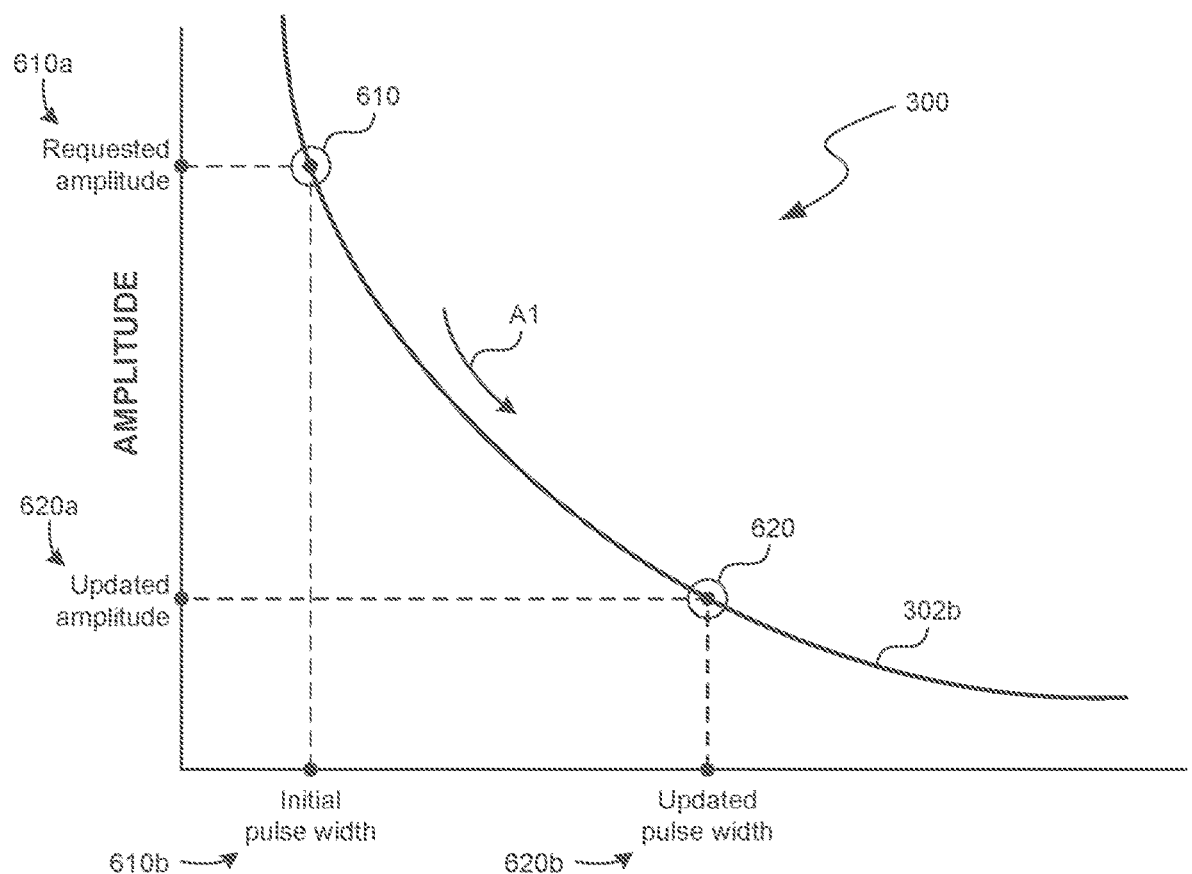
FIG. 6 graphically illustrates a process for updating signal amplitude and pulse width in accordance with an embodiment of the present technology.

Blocks 526 and 528 are discussed below with reference to FIG. 6. Block 526 includes determining an updated pulse width from the identified patient-specific curve. FIG. 6 illustrates a representative patient-specific curve 302*b* with the requested amplitude 610*a* and initial pulse width 610*b* identified as an initial therapy point 610. The updated amplitude 620*a* identified in block 524 is also indicated in FIG. 6. By proceeding along the patient-specific curve 302*b* as indicated by arrow A1, the program can identify an updated coordinate pair 620 having the updated amplitude 620*a* and a corresponding updated pulse width 620*b*. The therapy signal to be applied to the patient will be applied with the updated amplitude 620*a* and the updated pulse width 620*b*.

Block 528 determines, if necessary, an updated frequency. For example, if the updated pulse width is significantly greater than the initial pulse width, then the frequency may need to be decreased to account for the change. Alternatively, if an interpulse interval (e.g., the time period between adjacent pulses) is long enough to allow for an increase in pulse width without requiring a decrease in frequency, then the frequency can remain the same. In either case, a therapy signal with the updated amplitude, the updated pulse width, and the initial (or updated) frequency is then delivered at block 520.

The foregoing processes can be invoked, as needed, during the normal course of therapy. For example, the process described above with reference to FIG. 4 may be completed when the patient first begins receiving the therapy, and need not be repeated unless, for example, there is a basis for believing that the patient-specific correlation between pulse width and amplitude has shifted. The process described above with reference to FIG. 5 can be invoked periodically throughout the normal course of therapy. In another embodiment, the process described above with reference to FIG. 5 can first be invoked when the battery voltage (or other measure of available voltage) falls below a threshold level, and can then be invoked periodically until the battery is recharged. For current-based systems, it may be beneficial to determine the circuit impedance (block 522 in FIG. 5) relatively frequently to account for factors such as scar tissue build-up that may affect impedance.

One feature of at least some of the foregoing embodiments is that they can include using an established relationship between amplitude and pulse width (or duty cycle) to produce therapeutic results even when the voltage of the battery providing power for the electrical signal is reduced. An advantage of this arrangement is that it can eliminate the need for a boost circuit to deliver therapy, except as may be needed to identify the therapy delivery parameters. A corresponding advantage of this feature is that, because boost circuits can be inefficient, the amount of power lost as a result of delivering a therapy signal with a reduced battery output voltage can be reduced. Accordingly, the battery can last longer and can increase the time between battery charging events.

Another feature of at least some of the foregoing embodiments described above is that they may have particular applicability to therapies that do not produce paresthesia or other sensations in the patient. In particular, therapies that produce (and more generally rely on) paresthesia or other sensations may have those paresthesias or sensations change in nature, strength, and/or duration if the amplitude is shifted in the manner described above. Because it is expected that the amplitude for paresthesia-free therapy may be shifted without being sensed or detected by the patient, the foregoing process may be particularly beneficial in the context of therapies that do not produce paresthesia.

From the foregoing, it will be appreciated that specific embodiments of the presently disclosed technology have been described herein for purposes of illustration, but that various modifications may be made without deviating from the disclosed technology. For example, embodiments described above in the context of pulse width as a function of amplitude can apply as well for duty cycle as a function of amplitude. While the foregoing embodiments were described in the context of battery voltage and an associated current amplitude produced by an intermediate current source, in other embodiments, the technique can be applied in a voltage-amplitude-based system. In such embodiments, the amplitude axis of the curves shown in FIGS. 3 and 6 is voltage amplitude, and the pulse width can be determined directly from the curve (using the determined available voltage) without the intermediate step of calculating an updated amplitude based on the available voltage and circuit impedance.

In particular embodiments, representative current amplitudes for the therapy signal are from 0.1 mA to 20 mA, or 0.5 mA to 10 mA, or 0.5 mA to 7 mA, or 0.5 mA to 5 mA. Representative pulse widths range from about 10 microseconds to about 333 microseconds, about 10 microseconds to about 166 microseconds, 20 microseconds to about 100 microseconds, 30 microseconds to about 100 microseconds, and 30 microseconds to about 40 microseconds. Duty cycles can range from about 10% to about 100%, and in a particular duty cycle, signals are delivered for 20 seconds and interrupted for 2 minutes (an approximate 14% duty cycle). In other embodiments, these parameters can have other suitable values. For example, in at least some embodiments, the foregoing systems and methods may be applied to therapies that have frequencies outside the ranges discussed above (e.g., 1.5 kHz-100 kHz) but which also do not produce paresthesia. Representative therapies include therapies having relatively narrow pulse widths, as disclosed in U.S. Provisional Patent Application No. 61/901,255, filed Nov. 7, 2013 and incorporated herein by reference. Representative pulse widths (which can be delivered at frequencies above or below 1.5 kHz, depending upon the embodiment) include pulse widths from 10-50 microseconds, 20-40 microseconds, 25-35 microseconds, 30-35 microseconds, and 30 microseconds.

In still further embodiments, techniques generally similar to those described above may be applied to therapies that are directed to tissues other than the spinal cord. Representative tissues can include peripheral nerve tissue and/or brain tissue. In such contexts, the strength/duration relationships discussed above can be the same as or different than the relationships for spinal cord neurons, depending on the embodiment. The mechanism of action by which pain relief is obtained in any of the foregoing embodiments may include, but is not limited to, those described in U.S. Provisional Patent Application No. 61/833,392, filed Jun. 10, 2013 and incorporated herein by reference.

In other embodiments, other methodologies may be used to provide pain therapy to the patient, and in some instances, such methodologies may provide paresthesia-free pain relief. Representative methods asserted to provide paresthesia-free pain relief are disclosed in U.S. Pat. No. 8,224,453 to De Ridder and U.S. Pat. No. 8,380,318 to Kishawi et al. De Ridder discloses the use of "burst" stimulation (e.g., bursts of spikes at a frequency of up to 1,000 Hz, with a 0.1-1.0 millisecond interval between spikes, and a quiescent period of 1 millisecond to about 5 seconds between bursts) applied to the spinal cord. Kishawi et al. discloses applying a signal to the dorsal root ganglion at a frequency of less than 25 Hz, a pulse width of less than 120 microseconds and an amplitude of less than 500 microamps.

In several embodiments described above, a patient-specific relationship includes determining the amplitude and pulse width based on patient-specific testing. In other embodiments, where applicable, data from a pool of patients (e.g., patients with the same pain indication and/or other attributes) can be applied to a similarly situated patient without the need for a patient-specific test. Several embodiments were described above in the context of a battery (e.g., a lithium ion battery), and in other embodiments, the technology is applicable to other rechargeable power sources, e.g., capacitors.

Certain aspects of the technology described in the context of particular embodiments may be combined or eliminated in other embodiments. For example, selected process steps may be combined in some embodiments, and skipped in others. In particular embodiments, specific values described above (e.g., battery voltage, signal amplitude and the like) may be replaced by correlates of these values for data handling or other purposes. Certain of the processes described above may be carried out in an automated or semi-automated manner using the implanted signal generator 101 described above with reference to FIG. 1A. In other embodiments, some of the foregoing steps may be carried out by an external device (e.g., the physician programmer 117).

3.0 ADDITIONAL EMBODIMENTS

In one embodiment, there is provide a method for treating a patient, comprising: receiving an input corresponding to an available voltage for an implanted medical device; identifying a signal delivery parameter value of an electrical signal based on a correlation between values of the signal delivery parameter and signal delivery amplitudes, wherein the signal delivery parameter includes at least one of pulse width or duty cycle; and delivering an electrical therapy signal to the patient at the identified signal delivery parameter value using a voltage within a margin of the available voltage. The signal delivery parameter may be pulse width and/or duty cycle. The available voltage may be an output voltage of a battery that provides power for the electrical therapy signal. The method may further comprise: receiving at least one input corresponding to a target therapy amplitude and a target pulse width; determining that the available voltage is insufficient to supply a therapy signal at the target therapy amplitude and the target pulse width; identifying an updated therapy amplitude less than the target therapy amplitude; based at least in part on the updated therapy amplitude and the correlation, identifying an updated pulse width greater than the target pulse width; and delivering the electrical therapy signal to the patient at the updated therapy amplitude and the updated pulse width. The correlation may be patient-specific correlation, and wherein the method may further comprise establishing the correlation. Establishing the correlation may include establishing the correlation by producing paresthesia in the patient, and wherein delivering the electrical therapy signal does not produce paresthesia in the patient.

In another embodiment, there is provided a method for treating pain in a patient, comprising: establishing a patient-specific correlation between amplitudes and pulse widths by identifying at least one pulse width/amplitude pair that produces a detectable result in the patient; receiving at least one input corresponding to a target therapy amplitude, pulse width and frequency; determining an available voltage of a battery-powered implanted medical device; determining whether the available voltage is sufficient to direct a therapy signal to the patient at the target therapy amplitude, pulse width and frequency; and if the available voltage is not sufficient: determining an updated therapy amplitude and, based on the patient-specific correlation, an updated pulse width; and delivering an electrical therapy signal to the patient at the updated therapy amplitude and the updated pulse width; and if the available voltage is sufficient: delivering an electrical therapy signal to the patient at the target amplitude and pulse width. The detectable result may be a non-therapeutic result, and wherein the method may further comprise applying a correction factor to the patient-specific correlation to account for an expected difference between the non-therapeutic result and a target therapeutic result. The non-therapeutic result may include producing paresthesia in the patient and wherein the target therapeutic result may include producing pain relief without paresthesia in the patient. The method may further comprise determining if the updated pulse width can be delivered at the target frequency; and if the updated pulse width cannot be delivered at the target frequency, updating the target frequency. Establishing the patient-specific correlation may include using the at least one pulse width/amplitude pair to determine which of a plurality of pulse width/amplitude correlations applies to the patient. At least one pulse width/amplitude pair may be one of multiple pulse width/amplitude pairs used to determine which of the plurality of pulse width/amplitude correlations applies to the patient. Establishing the patient-specific correlation may include using data from other patients. Identifying the at least one pulse width/amplitude pair may be based at least in part on producing paresthesia in the patient with a signal having the pulse width and amplitude of the at least one pulse width/amplitude pair. Identifying the at least one pulse width/amplitude pair may be based at least in part on producing pain relief without producing paresthesia in the patient, with a signal having the pulse width and amplitude of the at least one pulse width/amplitude pair. Identifying the at least one pulse width/amplitude pair may be based at least in part on producing an evoked potential in the patient with a signal having the pulse width and amplitude of the at least one pulse width/amplitude pair. Determining the updated therapy amplitude may be based at least in part on the available voltage and on an impedance of a circuit via which the electrical therapy signal is delivered. The method may further comprise determining the impedance by: delivering an electrical therapy signal at the target amplitude and pulse width; determining a voltage across the circuit; and determining the impedance based on the target amplitude and the voltage across the circuit.

In another embodiment, there is provided a method of treating a patient by programming an implantable/external pulse generator to perform any one or more of the herein described methods, process, and/or sub-processes. In still another embodiment, there is provided a system for treating a patient comprising means for performing any one or more of the herein described methods, process, and/or sub-processes.

In another embodiment, there is provided a patient therapy system, comprising: (a) a pulse generator programmed with instructions for delivering an electrical therapy signal to a patient; (b) a processor operatively coupled to the pulse generator and programmed with instructions that, when executed: receive an input corresponding to an available voltage for the pulse generator; identify a signal delivery parameter value of an electrical signal based on a correlation between values of the signal delivery parameter and signal delivery amplitudes, wherein the signal delivery parameter includes at least one of pulse width or duty cycle; and direct the pulse generator to deliver an electrical therapy signal at the identified signal delivery parameter value using a voltage within a margin of the available voltage. The system may further comprise a signal delivery element coupled to the pulse generator to deliver the electrical therapy signal to a patient. The processor and the pulse generator may be housed in a patient-implantable device. The pulse generator may be housed in a patient-implantable device, and the processor may be housed in an external device. The system may further comprise a computer-readable medium coupled to the processor, and wherein the instructions are carried by the computer-readable medium. The pulse generator may be programmed with instructions for delivering the electrical therapy signal at a frequency of from 1.5 kHz to 100 kHz (or any range of the above-described frequencies). The pulse generator may be programmed with instructions for delivering the electrical therapy signal at a pulse width of from 10 microseconds to 333 microseconds (or any range of the above-described pulse widths). The processor may be programmed with instructions that, when executed: receive at least one input corresponding to a target therapy amplitude and a target pulse width; determine that the available voltage is insufficient to supply a therapy signal at the target therapy amplitude and the target pulse width; identify an updated therapy amplitude less than the target therapy amplitude; based at least in part on the updated therapy amplitude and the correlation, identify an updated pulse width greater than the target pulse width; and deliver the electrical therapy signal to the patient at the updated therapy amplitude and the updated pulse width.

In yet another embodiment, there is provide a patient therapy system, comprising: (a) an implantable housing; (b) a pulse generator carried within the housing and programmed with instructions for delivering an electrical therapy signal to a patient; (c) an implantable signal delivery element coupled to the pulse generator; (d) a battery carried within the housing and coupled to the pulse generator to provide power for the electrical therapy signal; and (e) a processor carried within the housing and operatively coupled to the pulse generator, the processor being programmed with instructions that, when executed: receive an input corresponding to an available voltage from the battery; identify a pulse width of an electrical signal based on a correlation between pulse widths and signal delivery amplitudes; and direct the pulse generator to deliver an electrical therapy signal at the identified pulse width value using a voltage within a margin of the available voltage. The processor may be programmed with instructions that, when executed: receive at least one input corresponding to a target current amplitude and a target pulse width; determine that the available voltage is insufficient to supply a therapy signal at the target current amplitude and the target pulse width; determine an impedance of a circuit via which the electrical therapy signal is delivered, the circuit including the patient; based at least in part on the impedance and the available voltage, determine an updated current amplitude less than the target current amplitude; based on the updated current amplitude and the correlation, identify an updated pulse width greater than the target pulse width. The pulse generator may be programmed with instructions for delivering the electrical therapy signal at a frequency of from 1.5 kHz to 100 kHz (or any of the above-described frequencies). The pulse generator may be programmed with instructions for delivering the electrical therapy signal at a pulse width of from 10 microseconds to 333 microseconds (or any of the above-described pulse widths).

While advantages associated with certain embodiments of the disclosed technology have been described in the context of those embodiments, other embodiments may also exhibit such advantages, and not all embodiments need necessarily exhibit such advantages to fall within the scope of the present technology. The following examples provide additional embodiments of the present technology.

To the extent the any of the foregoing patents, published applications, and/or any other materials incorporated herein by reference conflict with the present disclosure, the present disclosure controls.

I claim:

1. A method of programming a signal generator for stimulation therapy, the method comprising programming the signal generator to increase a signal delivery parameter of an electrical signal in response to a decrease in an available voltage, wherein the increase is based on a correlation between the signal delivery parameter and signal delivery amplitudes, and wherein the signal delivery parameter is a pulse width and/or a duty cycle.

2. The method of claim 1 wherein the available voltage is an output voltage of a battery that provides power for generating the electrical signal.

3. The method of claim 1 wherein the correlation between the signal delivery parameter and the signal delivery amplitudes is a patient-specific correlation.

4. The method of claim 1 wherein programming the signal generator to increase the signal delivery parameter includes programming the signal generator to automatically increase the signal delivery parameter in response to the decrease in the available voltage.

5. The method of claim 1 wherein the signal delivery parameter is the pulse width.

6. The method of claim 5 wherein the increased pulse width has a value within a pulse width range of from 10 microseconds to 333 microseconds.

7. The method of claim 1 wherein the signal delivery parameter is the duty cycle.

8. The method of claim 7 wherein the increased duty cycle has a value within a duty cycle range of from 10% to 100%.

9. The method of claim 1 wherein the electrical signal has a frequency in a frequency range of from 1.5 kHz to 100 kHz.

10. The method of claim 1 wherein the electrical signal does not induce paresthesia in the patient.

11. A system for providing stimulation therapy to a patient, the system comprising:
  a signal generator programmed to deliver an electrical signal to the patient;
  a processor; and
  a memory storing instructions that, when executed by the processor, cause the signal generator to:
    increase a signal delivery parameter of the electrical signal in response to a decrease in an available voltage,
    wherein the increase is based on a correlation between the signal delivery parameter and signal delivery amplitudes, and
    wherein the signal delivery parameter is a pulse width and/or a duty cycle.

12. A method of programming a signal generator for stimulation therapy, the method comprising:
  programming the signal generator to, in response to a determination that an available voltage is insufficient to deliver an electrical signal at a target therapy amplitude and a target signal delivery parameter, identify (a) an updated therapy amplitude that is less than the target therapy amplitude, and (b) an updated signal delivery parameter that is greater than the target signal delivery parameter, wherein the signal delivery parameter includes a pulse width and/or a duty cycle.

13. The method of claim 12 wherein programming the signal generator further comprises programming the signal generator to deliver the electrical signal at the updated therapy amplitude and the updated signal delivery parameter.

14. The method of claim 12 wherein the available voltage is an output voltage of a battery that provides power for generating the electrical signal.

15. The method of claim 12 wherein the updated therapy amplitude and the updated signal delivery parameter are identified based at least in part on a predetermined correlation between amplitude and the signal delivery parameter.

16. The method of claim 15 wherein the correlation is a patient-specific correlation.

17. The method of claim 12 wherein the signal delivery parameter is the pulse width.

18. The method of claim 17 wherein the updated pulse width has a value within a pulse width range of from 10 microseconds to 333 microseconds.

19. The method of claim 12 wherein the signal delivery parameter is the duty cycle.

20. The method of claim 19 wherein the updated duty cycle has a value within a duty cycle range of from 10% to 100%.

21. The method of claim 12 wherein the electrical signal has a frequency in a frequency range of from 1.5 kHz to 100 kHz.

22. The method of claim 12 wherein the electrical signal does not induce paresthesia in the patient.

23. A system for providing stimulation therapy to a patient, the system comprising:
  a signal generator programmed to deliver an electrical signal to the patient;
  a processor; and
  a memory storing instructions that, when executed by the processor, cause the signal generator to:
    identify, in response to a determination that an available voltage is insufficient to deliver the electrical signal at a target therapy amplitude and a target signal delivery parameter, (a) an updated therapy amplitude that is less than the target therapy amplitude, and (b) an updated signal delivery parameter that is greater than the target signal delivery parameter, wherein the signal delivery parameter includes a pulse width and/or a duty cycle; and
    deliver the electrical signal at the updated therapy amplitude and with the updated signal delivery parameter.

* * * * *

UNITED STATES PATENT AND TRADEMARK OFFICE
CERTIFICATE OF CORRECTION

PATENT NO. : 11,766,566 B2
APPLICATION NO. : 17/114314
DATED : September 26, 2023
INVENTOR(S) : Jon Parker It is certified that error appears in the above-identified patent and that said Letters Patent is hereby corrected as shown below:

On the Title Page

In item (57), in Column 2, in "Abstract", Line 9, delete "signal deliver amplitudes." and insert -- signal delivery amplitudes. --.

In item (57), in Column 2, in "Abstract", Lines 9-10, delete "signal deliver parameter" and insert -- signal delivery parameter --.

On the page 2, in Column 1, Item (56) under "U.S. Patent Documents", Line 22, delete "Hirsch" and insert -- Hirschi --.

On the page 3, in Column 2, Item (56) under "U.S. Patent Documents", Line 24, after "Fang" insert -- et al. --.

On the page 3, in Column 2, Item (56) under "U.S. Patent Documents", Line 30, after "King" insert -- et al. --.

On the page 4, in Column 1, Item (56) under "U.S. Patent Documents", Line 25, after "Parker" insert -- et al. --.

On the page 4, in Column 2, Item (56) under "Other Publications", Line 11, delete "European Extended Search Report (EPSR)" and insert -- European Extended Search Report (EESR) --.

In the Specification

In Column 1, Line 13, delete "10,176,062, file" and insert -- 10,173,062, filed --.

In Column 1, Line 17, after "Application" insert -- No. --.

In Column 7, Line 1, delete "mm." and insert -- mm --.

Signed and Sealed this
Nineteenth Day of December, 2023

Katherine Kelly Vidal
*Director of the United States Patent and Trademark Office*